US008556893B2

(12) United States Patent
Potter

(10) Patent No.: US 8,556,893 B2
(45) Date of Patent: Oct. 15, 2013

(54) MEDICAL CATHETER ASSEMBLY WITH DEFLECTION PULL RING AND DISTAL TIP INTERLOCK

(75) Inventor: Daniel J. Potter, Stillwater, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/453,525

(22) Filed: Apr. 23, 2012

(65) Prior Publication Data

US 2012/0203170 A1    Aug. 9, 2012

Related U.S. Application Data

(63) Continuation of application No. 11/963,441, filed on Dec. 21, 2007, now Pat. No. 8,162,934.

(51) Int. Cl.
*A61B 18/18* (2006.01)

(52) U.S. Cl.
USPC ............................................ 606/41; 604/95.05

(58) Field of Classification Search
USPC .......... 606/41, 32–34, 47, 50, 129; 604/95.01
See application file for complete search history.

(56) References Cited

U.S. PATENT DOCUMENTS

| | | | |
|---|---|---|---|
| 5,273,535 A | 12/1993 | Edwards et al. |
| 5,389,073 A | 2/1995 | Imran |
| 5,391,147 A | 2/1995 | Imran et al. |
| 5,431,168 A | 7/1995 | Webster et al. |
| 5,462,527 A | 10/1995 | Stevens-Wright et al. |
| 5,478,330 A | 12/1995 | Imran et al. |
| 5,533,967 A | 7/1996 | Imran |
| 5,545,200 A | 8/1996 | West et al. |
| 5,588,964 A | 12/1996 | Imran et al. |
| 5,666,970 A | 9/1997 | Smith |
| 5,882,333 A | 3/1999 | Schaer et al. |
| 5,968,052 A | 10/1999 | Sullivan et al. |
| 6,113,572 A | 9/2000 | Gailey et al. |
| 6,926,669 B1 | 8/2005 | Stewart et al. |
| 7,229,437 B2 | 6/2007 | Johnson et al. |
| 7,632,265 B2 | 12/2009 | Hauck et al. |
| 7,974,674 B2 | 7/2011 | Hauck et al. |
| 2003/0078571 A1 | 4/2003 | Sliwa, Jr. et al. |
| 2006/0015096 A1 | 1/2006 | Hauck et al. |
| 2007/0016167 A1 | 1/2007 | Smith et al. |
| 2007/0250056 A1 | 10/2007 | Vanney |
| 2007/0270679 A1 | 11/2007 | Nguyen et al. |

FOREIGN PATENT DOCUMENTS

| | | |
|---|---|---|
| EP | 0982047 | 5/2000 |
| EP | 1205208 | 5/2002 |
| WO | 9729801 | 8/1997 |
| WO | 2009082570 A1 | 7/2009 |

OTHER PUBLICATIONS

International Search Report and Written Opinion for PCT/US2008/083731 mailed Jan. 9, 2009.

*Primary Examiner* — Linda Dvorak
*Assistant Examiner* — Amanda Scott
(74) *Attorney, Agent, or Firm* — Dykema Gossett PLLC

(57) ABSTRACT

A catheter assembly comprises a deflectable catheter shaft comprising a distal end and a lumen extending therethrough. The catheter assembly further comprises least one pull wire comprising a distal portion comprising a side and a distal end, wherein the side comprises a first side portion and a second side portion. The catheter assembly further comprises a distal pull assembly operatively coupled to the at least one pull wire. The distal pull assembly comprises a longitudinal axis, a first surface, and a second surface. The first side portion of the at least one pull wire is adjacent to the first surface of the distal pull assembly, and the second side portion of the at least one pull wire is adjacent to the second surface of the distal pull assembly.

17 Claims, 4 Drawing Sheets

MEDICAL CATHETER ASSEMBLY WITH DEFLECTION PULL RING AND DISTAL TIP INTERLOCK

CROSS-REFERENCE TO RELATED APPLICATIONS

This application is a continuation of U.S. application Ser. No. 11/963,441, filed 21 Dec. 2007 (the '441 application), now pending. The '441 application is hereby incorporated by reference as though fully set forth herein.

BACKGROUND OF THE INVENTION a. Field of the Invention

The present invention relates to medical catheter assemblies, and in particular to medical catheter assemblies which utilize a deflection pull ring adjacent a distal tip at the distal end of the catheter shaft to bend the deflectable catheter shaft and move the distal tip in a desired direction.

b. Background Art

Medical catheter assemblies used in the diagnosis or treatment of various medical abnormalities are in common use in medical facilities throughout the world. They generally include a deflectable catheter shaft that can be inserted in and extended along a suitable vein or artery of person being diagnosed or treated to a desired site; a handle actuator which supports a proximal end of the catheter shaft; a distal tip which is connected to the distal end of the catheter shaft and which includes a specialized tip element for the appropriate diagnosis or treatment; and a pull ring assembly which includes a pull ring near the distal end of the catheter shaft and pull wires which extend from the pull ring through the catheter shaft back to the handle actuator for tilting or rocking the pull ring upon manual operation of the handle actuator and consequential pulling of the pull wires, i.e., for deflecting a distal end portion of the catheter shaft with distal tip in a desired direction.

Ablation catheter assemblies are a category of medical catheter assembly used to ablate tissue, e.g., in the treatment of heart malfunctions. They can be irrigated (discharge ablation fluid in addition to ablation energy) or non-irrigated (discharge of ablation energy but not fluid). The distal tip will include a tip electrode as the specialized tip element and an energy source will be connected to their handle actuator to supply energy to the tip electrode. In irrigated catheter assemblies a fluid manifold is attached to, or is one-piece with, the tip electrode, and a fluid source is attached to their handle actuator to supply ablation fluid thereto. In either, the distal tip can include a mounting shaft which cooperates with the distal end of the adjacent deflectable catheter shaft for connection thereto.

It has been found that the operation of such medical catheter assemblies, including irrigated or non-irrigated ablation catheter assemblies, can become compromised over time with creeping of the pull ring towards the handle actuator (and away from the distal tip) due to repeated tilting or rocking thereof by the pull wires. In addition, failure of the medical catheter assemblies can occur with separation of the pull wires from the pull rings of the pull ring assemblies due to stress failure of the braze or weld joints therebetween.

It is thus an object of the present invention to provide a medical catheter assembly (including an irrigated or non-irrigated ablation catheter assembly) which is constructed such that creeping of the pull ring towards the handle actuator (and away from the distal tip) is prevented.

It is another object of the present invention to provide a medical catheter assembly (including an irrigated or non-irrigated catheter assembly) which is constructed such that stress on the connecting joints between the pull wires and pull ring is reduced, reducing failure of medical catheter assembly due to failure of the pull ring assembly.

BRIEF SUMMARY OF THE INVENTION

A catheter assembly can comprise a deflectable catheter shaft comprising a distal end and a lumen extending therethrough; at least one pull wire comprising a distal portion comprising: a side and a distal end, wherein the side comprises a first side portion and a second side portion; and a distal pull assembly operatively coupled to the at least one pull wire. The distal pull assembly can comprise a longitudinal axis; a first surface; and a second surface. The first side portion of the at least one pull wire can be adjacent to the first surface of the distal pull assembly. The second side portion of the at least one pull wire can be adjacent to the second surface of the distal pull assembly. In accordance with some embodiments of the invention, the first side portion of the at least one pull wire can contact and/or be in engagement with the first surface of the distal pull assembly and the second side portion of the at least one pull wire can contact and/or be in engagement with the second surface of the distal pull assembly.

In accordance with some embodiments of the invention, the second surface of the distal pull assembly is substantially transverse to the first surface of the distal pull assembly. The first surface can comprise a radially facing surface and the second surface can comprise a substantially distally facing surface in accordance with some embodiments of the invention. The catheter assembly can further comprise a distal tip at the distal end of the catheter shaft and including a tip element and a mounting shaft.

The at least one pull wire can extend through the catheter shaft along the longitudinal axis of the distal pull assembly toward the distal end and then extend at least in part in a direction that is non-parallel to the longitudinal axis of the distal pull assembly. The at least one pull wire can extend through the catheter shaft along the longitudinal axis of the pull assembly toward the distal end and then at least a portion of the pull wire can extend distal of the second surface of the distal pull assembly. Pulling of the at least one pull wire can directly impart force to the distal pull assembly to bend the catheter shaft. The catheter assembly can comprise two pull wires attached to diametrically opposite locations on the distal pull assembly in accordance with some embodiments of the invention. The at least one pull wire can be flat along at least a portion of its length in accordance with some embodiments of the invention. At least a portion of the at least one pull wire can be adjacent to an outer surface of the distal pull assembly in accordance with some embodiments of the invention. The at least one pull wire can be configured such that when force is applied to the at least one pull wire in a proximal direction, the pull assembly deflects.

A catheter assembly can comprise a deflectable catheter shaft comprising a distal end and a lumen extending therethrough; at least one pull wire comprising a distal portion comprising: a side, wherein the side comprises a first side portion and a second side portion; and a distal end; and a distal pull assembly comprising: a longitudinal axis; a first surface comprising a radially facing surface; and a second surface comprising at least in part a substantially distally facing surface. The first side portion of the at least one pull wire can be adjacent to the first surface of the distal pull assembly. The second side portion of the at least one pull wire can be adjacent to the second surface of the distal pull assembly. The at least one pull wire can extend through the catheter shaft along the longitudinal axis of the distal pull assembly toward the distal end and then extend at least in part in a direction that is non-parallel to the longitudinal axis of the distal pull assembly. At least a portion of the at least one pull wire can extend distal of the second surface of the distal pull assembly. The at least one pull wire and the distal pull assembly are configured such that pulling of said pull wire can directly impart force to the distal pull assembly to bend the catheter shaft.

The invention will be better understood by reference to the attached drawings, taken in conjunction with the following discussion.

DETAILED DESCRIPTION OF THE INVENTION

Figure 1:
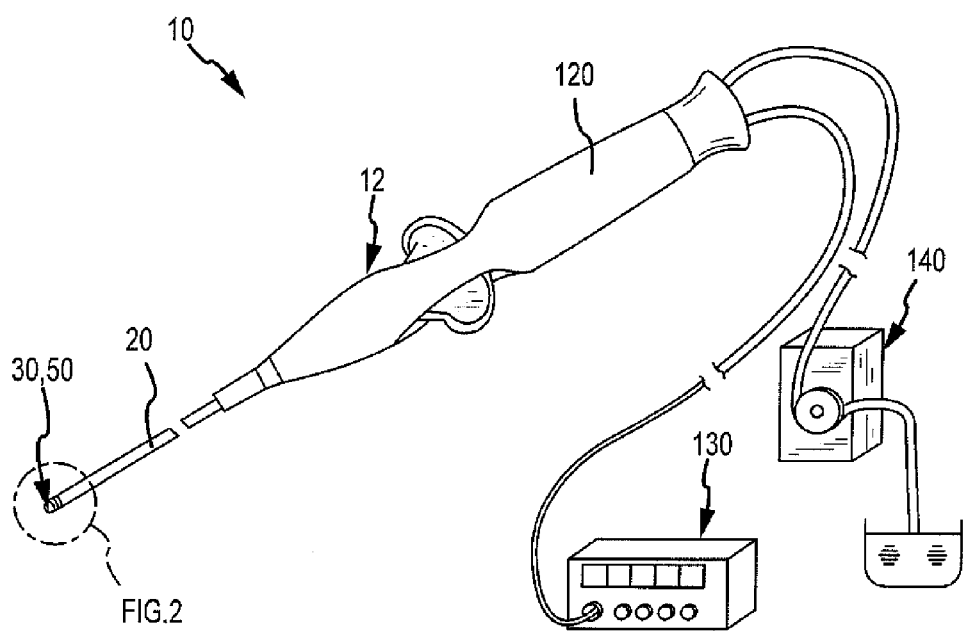
FIG. 1 is an isometric view of an irrigated ablation catheter system that includes an ablation catheter assembly, an energy source and a fluid source in accordance with a first embodiment of the present invention.

FIG. 1 shows an irrigated ablation catheter system 10 according to a preferred embodiment of the present invention. It includes an irrigated ablation catheter assembly 12 connected to an energy source 130 and a fluid source 140.

The irrigated ablation catheter assembly 12 includes a catheter 20, a handle actuator 120 which supports a proximate end of the catheter 20, a distal tip 30 attached to a distal end of the catheter and a pull ring assembly 50.

Figure 2:
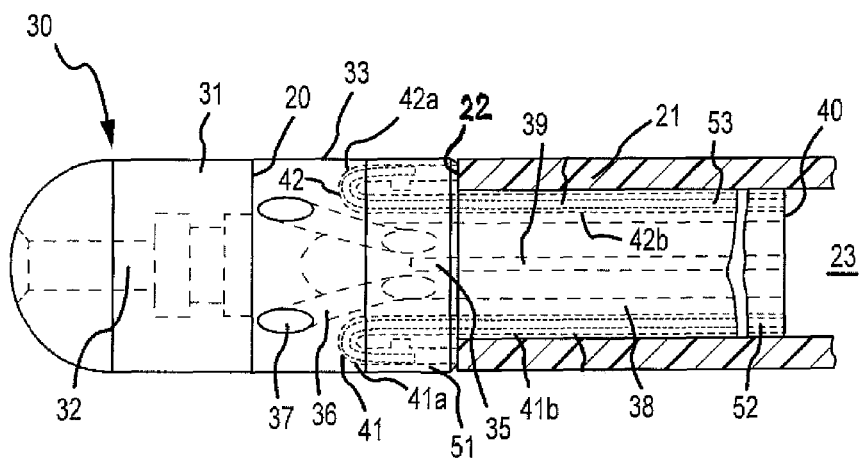
FIG. 2 is an enlarged side view of the distal end portion of the deflectable ablation catheter shaft, the pull ring assembly and distal tip of the catheter of FIG. 1.
Figure 3:
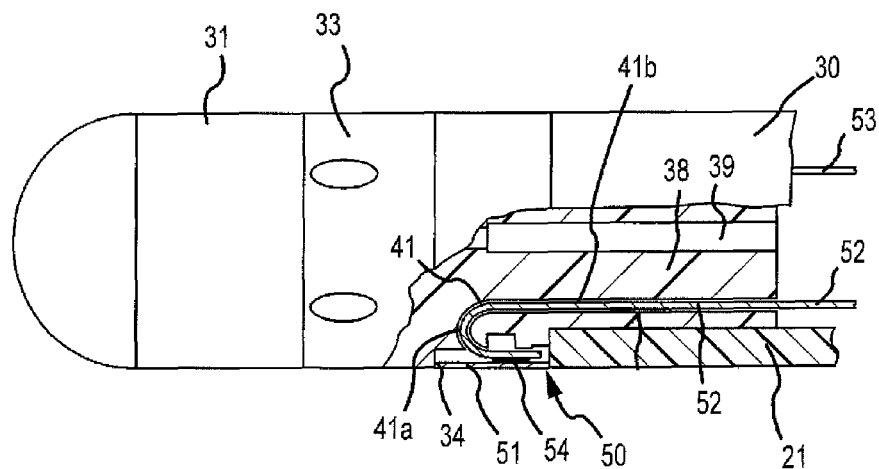
FIG. 3 is an enlarged detail of FIG. 2.

As seen in FIGS. 2 and 3, the distal tip 30 includes a tip electrode 31, a fluid manifold 33 and a mounting shaft 38. The fluid manifold 33 is attached to the tip electrode with adhesive (in another embodiment the fluid manifold and the tip electrode can be one piece). The mounting shaft 38 is one piece with the fluid manifold 33, and it extends into the hollow interior 23 of the catheter shaft 21. It has a smaller diameter than that of the fluid manifold (which is cylindrical in shape), thus leaving an outer annular ledge 34 on a rear face of the fluid manifold. The mounting shaft defines a central axial passageway 39 for ablation fluid supplied by a fluid delivery tube (not shown) in the catheter shaft. The fluid manifold 33 defines a central axial passageway 35 which is an extension of the central axial passageway 39, and delivery channels 36 that extend from the axial passageway 35 to orifices 37 spaced around its periphery (in another embodiment only one delivery channel leading to one orifice is employed). Fluid supplied to the axial passageway 39 in the mounting shaft will flow to the axial passageway 35 and then through delivery channels 36 to orifices 37 for discharge around the distal tip. The tip electrode 31 includes a channel 32 which will deliver fluid from the axial passageway 35 to its distal end. It can be made of platinum or other well-known materials.

Guide channels 41 and 42 are provided in the mounting shaft 38 at diametrically-opposed locations. The guide channel 41 includes a curved section 41a and a rectilinear section 41b. The curved section 41a has an inlet opening in the outer surface of the mounting shaft near fluid manifold 33 and the rectilinear section 41b has an outlet opening at the free end 40 of the mounting shaft. The guide channel 42 has corresponding sections 42a and 42b. The pull wires of the pull ring assembly respectively extend through these guide channels.

The pull ring assembly 50 includes a pull ring 51 and pull wires 52 and 53 attached to diametrically opposite locations on an inner face of the pull ring by a solder or weld joint 54. The pull wires are flat along at least a portion of their length, in particular at their distal ends, otherwise round. Other configurations are possible. The pull ring 51 is positioned between the distal end 22 of the catheter shaft 21 and the outer annular ledge 34 of the fluid manifold, and the pull wires extend from the pull ring toward the fluid manifold and then loop back respectively in and through the guide channels 41 and 42 to the handle actuator 120. Pulling of the pull wires 52, 53 by the handle actuator during use of the catheter assembly will cause the pull ring to tilt or rock, thereby bending the catheter shaft 21, and also pulling the pull ring 51 toward contact with the outer annular ledge 34 of the fluid manifold 33.

Figure 4:
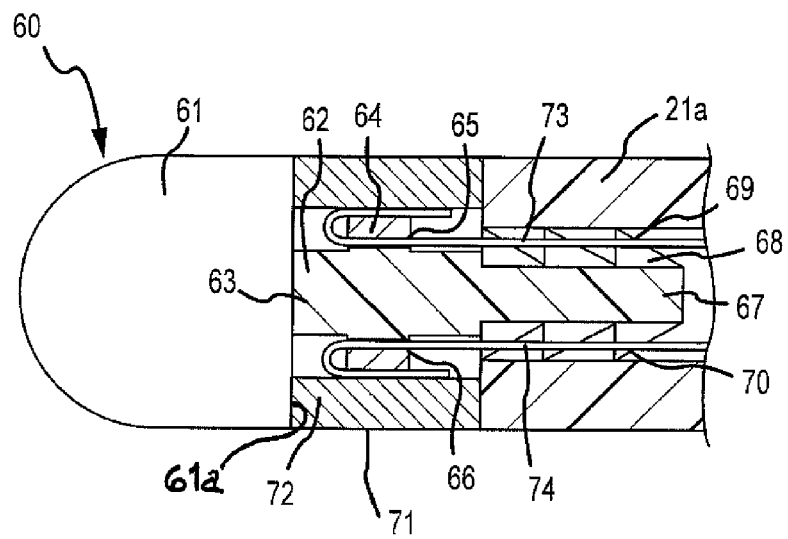
FIG. 4 is a side view, partly in section, of a distal end portion of a catheter shaft, a pull ring assembly and a distal tip according to a second embodiment of the invention.

Turning now to the embodiment of FIG. 4, the distal tip 60 includes a specialized tip element 61 (in an ablation catheter assembly a tip electrode) and a mounting shaft 62 having a distal portion 63 and a proximal portion 67. The proximal portion 67 includes barbs 68 in its outer surface to grip the distal end of the catheter shaft 21a, and axial grooves (guide channels) 69, 70 at diametrically opposed locations. The barbs could be replaced by surface protrusions of varying configurations. The distal portion 63 includes an annular flange 64 having axial guide channels 65 and 66 therethrough which are aligned with axial grooves 69 and 70. The pull ring 72 of pull ring assembly 71 is positioned between the distal end of catheter shaft 21a and an outer annular ledge 61a of the tip element 61, and the pull wires 73 and 74 attached to diametrically opposed locations on its inner face extend toward the tip electrode and then loop back through respective guide channels 65, 69 and 66, 70 to a handle actuator.

Figure 5:
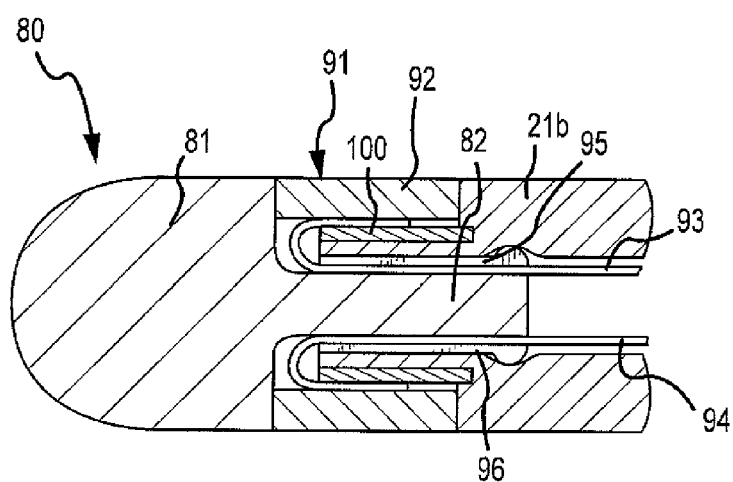
FIGS. 5 and 6 show side views of third and fourth embodiments.

In the embodiment of FIG. 5, a compression ring 100 compresses a distal end portion of catheter shaft 21b against an outer surface of mounting shaft 82, which is one-piece with the tip element 81, and the pull wires 93 and 94 of pull ring assembly 91 extend toward the tip element 81 of distal tip 80 and then loop back toward the catheter shaft and pass through respective axial grooves (guide channels) 95, 96 in the outer surface of the mounting shaft. The compression ring 100 has a generally rectangular cross-section.

Figure 6:
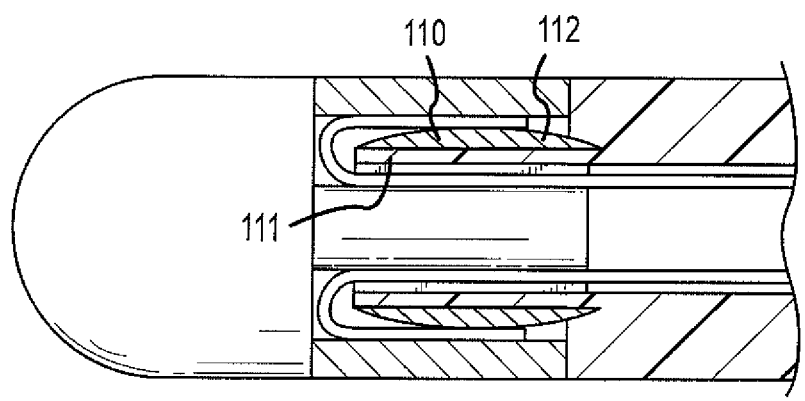

In the embodiment of FIG. 6, which is similar to that of FIG. 5, the compression ring 110 defines a generally flat surface 111 facing inwardly toward the mounting shaft and a generally convex outwardly facing surface 112.

Although a detailed explanation of various embodiments of the invention have been provided, changes therein can be made and still fall within the scope of the present invention. For example, the pull ring assembly may include more than two pull wires attached to the pull ring around its circumference, with corresponding guide channels provided in the distal tip to guide the individual pull wires first toward the tip element of the distal tip and then to loop back to the handle actuator. Also, the compression ring as shown in FIGS. 5 and 6 could have shapes other than those specifically depicted.

What is claimed is:
1. A catheter assembly comprising:
  a deflectable catheter shaft comprising a distal end and a lumen extending therethrough;
    at least one pull wire comprising a distal portion comprising:

a side, wherein the side comprises a first side portion and a second side portion; and
a distal end; and
a distal pull assembly operatively coupled to the at least one pull wire, the distal pull assembly comprising:
a longitudinal axis;
a first surface; and
a second surface, wherein the first side portion of the at least one pull wire is adjacent to the first surface of the distal pull assembly and wherein the second side portion of the at least one pull wire is adjacent to the second surface of the distal pull assembly.

2. The catheter assembly of claim 1, wherein the second surface of the distal pull assembly is substantially transverse to the first surface of the distal pull assembly.

3. The catheter assembly of claim 1, wherein the first surface comprises a radially facing surface.

4. The catheter assembly of claim 1, wherein the second surface comprises a substantially distally facing surface.

5. The catheter assembly of claim 1, further comprising a distal tip at the distal end of the catheter shaft and including a tip element and a mounting shaft.

6. The catheter assembly of claim 1, wherein the at least one pull wire extends through the catheter shaft along the longitudinal axis of the distal pull assembly toward the distal end and then extends at least in part in a direction that is non-parallel to the longitudinal axis of the distal pull assembly.

7. The catheter assembly of claim 1, wherein the at least one pull wire extends through the catheter shaft along the longitudinal axis of the pull assembly toward the distal end and then at least a portion of the pull wire extends distal of the second surface of the distal pull assembly.

8. The catheter assembly of claim 1, wherein pulling of the at least one pull wire directly imparts force to the distal pull assembly to bend the catheter shaft.

9. The catheter assembly of claim 1, wherein the catheter assembly comprises two pull wires attached to diametrically opposite locations on the distal pull assembly.

10. The catheter assembly of claim 1, wherein the at least one pull wire is flat along at least a portion of its length.

11. The catheter assembly of claim 1, wherein at least a portion of the at least one pull wire is adjacent to an outer surface of the distal pull assembly.

12. The catheter assembly of claim 1, wherein the at least one pull wire is configured such that when force is applied to the at least one pull wire in a proximal direction, the pull assembly deflects.

13. The catheter assembly of claim 1, wherein the first side portion of the at least one pull wire contacts the first surface of the distal pull assembly and wherein the second side portion of the at least one pull wire contacts the second surface of the distal pull assembly.

14. The catheter assembly of claim 1, wherein the first side portion of the at least one pull wire is in engagement with the first surface of the distal pull assembly and wherein the second side portion of the at least one pull wire is in engagement with the second surface of the distal pull assembly.

15. The catheter assembly of claim 1, further comprising a passageway extending through said deflectable catheter shaft, said passageway configured to provide delivery of an irrigation fluid from a fluid source to said distal end.

16. A catheter assembly comprising:
a deflectable catheter shaft comprising a distal end and a lumen extending therethrough;
at least one pull wire comprising a distal portion comprising:
a side, wherein the side comprises a first side portion and a second side portion; and
a distal end; and
a distal pull assembly comprising:
a longitudinal axis;
a first surface comprising a radially facing surface; and
a second surface comprising at least in part a substantially distally facing surface, wherein the first side portion of the at least one pull wire is adjacent to the first surface of the distal pull assembly and wherein the second side portion of the at least one pull wire is adjacent to the second surface of the distal pull assembly,
wherein the at least one pull wire extends through the catheter shaft along the longitudinal axis of the distal pull assembly toward the distal end and then extends at least in part in a direction that is non-parallel to the longitudinal axis of the distal pull assembly,
wherein at least a portion of the at least one pull wire extends distal of the second surface of the distal pull assembly, and
wherein the at least one pull wire and the distal pull assembly are configured such that pulling of the at least one pull wire directly imparts force to the distal pull assembly to bend the catheter shaft.

17. The catheter assembly of claim 16, further comprising a passageway extending through said deflectable catheter shaft, said passageway configured to provide delivery of an irrigation fluid from a fluid source to said distal end.

* * * * *